US012333721B2

(12) United States Patent
Chen (10) Patent No.: US 12,333,721 B2
(45) Date of Patent: *Jun. 17, 2025

(54) TISSUE IDENTIFICATION AND CLASSIFICATION BASED ON VIBRATIONAL SIGNATURES (71) Applicant: Baxton Chen, San Marino, CA (US)

(72) Inventor: Baxton Chen, San Marino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/614,316

(22) Filed: Mar. 22, 2024

(65) Prior Publication Data
US 2024/0257347 A1    Aug. 1, 2024

Related U.S. Application Data (63) Continuation of application No. 17/222,336, filed on Apr. 5, 2021, now Pat. No. 11,967,065.

(51) Int. Cl.
G06T 7/00 (2017.01)
A61B 8/00 (2006.01)

(52) U.S. Cl.
CPC .......... G06T 7/0012 (2013.01); A61B 8/4427 (2013.01); A61B 8/461 (2013.01); A61B 2562/0219 (2013.01); G06T 2207/10132 (2013.01); G06T 2207/20081 (2013.01); G06T 2207/20084 (2013.01)

(58) Field of Classification Search
CPC .......... G16H 50/20; A61B 2018/00434; A61B 5/0051; A61B 5/1075; A61B 5/1128; A61B 5/486; A61B 2562/0204; A61B 5/0057; A61B 8/4427; A61B 8/461; A61B 2562/0219; G06F 18/20; G06F 18/217; G06N 20/00; G06N 3/02; G06V 10/776; G06T 7/0012; G06T 2207/10132; G06T 2207/20081; G06T 2207/20084
See application file for complete search history.

(56) References Cited

U.S. PATENT DOCUMENTS

| 5,086,775 | A | * | 2/1992 | Parker | G01N 29/46 600/453 |
| 6,264,609 | B1 | | 7/2001 | Herrington | |
| 11,967,065 | B2 | * | 4/2024 | Chen | A61B 8/461 |
| 2003/0220556 | A1 | * | 11/2003 | Porat | A61B 5/4312 600/407 |

(Continued)

FOREIGN PATENT DOCUMENTS

WO    2014150780    9/2014
WO    WO-2014150780 A2 * 9/2014 ........... A61B 5/1121

(Continued)

Primary Examiner — Aaron W Carter
Assistant Examiner — Courtney Joan Nelson
(74) Attorney, Agent, or Firm — Loeb & Loeb LLP (57) ABSTRACT A tissue analysis system and method may use a vibration signature of an unknown tissue to identify the tissue. The system and method may compare the vibration signature to a plurality of vibration signatures for known tissues, and determine if a match between the vibration signature of the tissue and at least one of the plurality of vibration signatures for known tissues is present. The system and method may then determine an identity of the tissue based on the known identity of the known tissue having the matching vibration signature and optimize the vibration signature.

20 Claims, 9 Drawing Sheets (56) References Cited

U.S. PATENT DOCUMENTS

2010/0286522 A1* 11/2010 Beach ...................... A61B 8/08
                                                          600/441
2017/0265807 A1    9/2017 Stopek

FOREIGN PATENT DOCUMENTS

WO         2020020770      1/2020
WO    WO-2020020770 A1 *  1/2020  ........... A61B 8/5207

* cited by examiner

| Tissue Identity | Classification | Vibration Signature |
|---|---|---|
| Liver | Normal | ~28 |
| | ⋯ | |
| Lung | Cancerous | ~28 |

TISSUE IDENTIFICATION AND CLASSIFICATION BASED ON VIBRATIONAL SIGNATURES

RELATED APPLICATIONS

This application is a continuation of U.S. application Ser. No. 17/222,336 filed Apr. 5, 2021, entitled "TISSUE IDENTIFICATION AND CLASSIFICATION BASED ON VIBRATIONAL SIGNATURES", reference of which is hereby incorporated by reference in its entirety.

TECHNICAL FIELD

Embodiments discussed herein generally relate to systems and methods for tissue identification and classification based on tissue vibrational signatures in response to ultrasound stimulation.

BACKGROUND

Ultrasound is one of the most common methods for medical imaging. It is a rapid and noninvasive method to examine body anatomy that does not rely on ionizing radiation like X-rays or computerized axial tomography (CAT) scans. During ultrasound examination, an ultrasound probe is placed on the skin to project penetrating ultrasound waves through the underlying tissues, and images of the reflected sound waves are analyzed to identify and examine the underlying anatomical structures. While effective, the analysis of ultrasound images requires extensive training and experience, and the process of tissue identification and characterization may be subjective and inexact. For example, studies have shown that even experienced radiologists may miss up to 32% of liver cirrhosis during ultrasound examinations. See Kelley et al. Gastroenterol. Hepatol (N Y). 2018 June; 14(6): 367-373.

Thus, there is a need for more objective and reliable approaches for identifying and classifying body tissue. The present disclosure provides a technical solution for this need.

SUMMARY

Embodiments disclosed herein provide a technical solution for identifying and classifying tissue in a reliable and objective manner through an approach that relies on the tissue's characteristic vibration signal in response to ultrasound stimulation. In one embodiment, a system for identifying tissue may include an ultrasound device having a transducer configured to project ultrasound waves at tissue to cause the tissue to vibrate and produce a vibration signature, a vibration detector configured to detect the vibration signature of the tissue, and a database storing a plurality of vibration signatures each being linked in the database with a known tissue of a known identity. The system may further include a signal analysis processor in communication with the vibration detector and the database. The signal analysis processor may be configured according to computer-executable instructions for comparing the vibration signature of the tissue with the plurality of vibration signatures stored in the database, determining if a match is present between the vibration signature of the tissue and at least one of the stored vibration signatures if a similarity between the vibration signature of the tissue and the stored vibration signature is above a predetermined threshold and, if the match is present, determining an identity of the tissue based on the known identity of the tissue having the matching stored vibration signature.

In another embodiment, a method for identifying tissue may include stimulating tissue of an unknown identity with ultrasound waves produced by an ultrasound device to cause the tissue to vibrate and produce a vibration signature, detecting the vibration signature with a vibration detector, and communicating the detected vibration signature to a signal analysis processor. At the signal analysis processor, the method may further include accessing a signature library storing a plurality of vibration signatures each linked to one of a plurality of different known tissues having a known identity, comparing the vibration signature of the tissue to the stored vibration signatures of the signature library to identity at least one match in which a similarity between the vibration signature of the tissue and one of the stored vibration signatures is above a predetermined threshold, determining an identity of the tissue based on the known identity of the known tissue having the matching stored vibration signature, and outputting the determined identity of the tissue to a display interface of a computer device.

BRIEF DESCRIPTION OF THE DRAWINGS

The disclosure may be better understood by reference to the detailed description when considered in connection with the accompanying drawings. The components in the figures are not necessarily to scale, emphasis instead being placed upon illustrating the principles of the disclosure.

DETAILED DESCRIPTION

Applicant has discovered that tissue layers, in addition to reflecting probing ultrasound waves, also absorb some of the ultrasound energy and vibrate according to the tissue's inherent structural integrity and density to produce characteristic vibration signatures. Based on this finding, a novel system and method has been devised that relies on such characteristic vibration signatures to identify and classify tissues under ultrasound examination. The system and method of the present disclosure may be applied to resolve tissue type not only according to its anatomical structure (e.g., heart, liver, lung, skeletal muscle, etc.), but also according to its condition or state (e.g., normal/healthy, abnormal, diseased, cancerous, congenitally defective, injured, damaged, etc.). Abnormal, diseased, injured, damaged, or defective tissues of a certain tissue identity may exhibit a vibrational signature that is different compared to normal or healthy tissue of the same identity.

Figure 1:
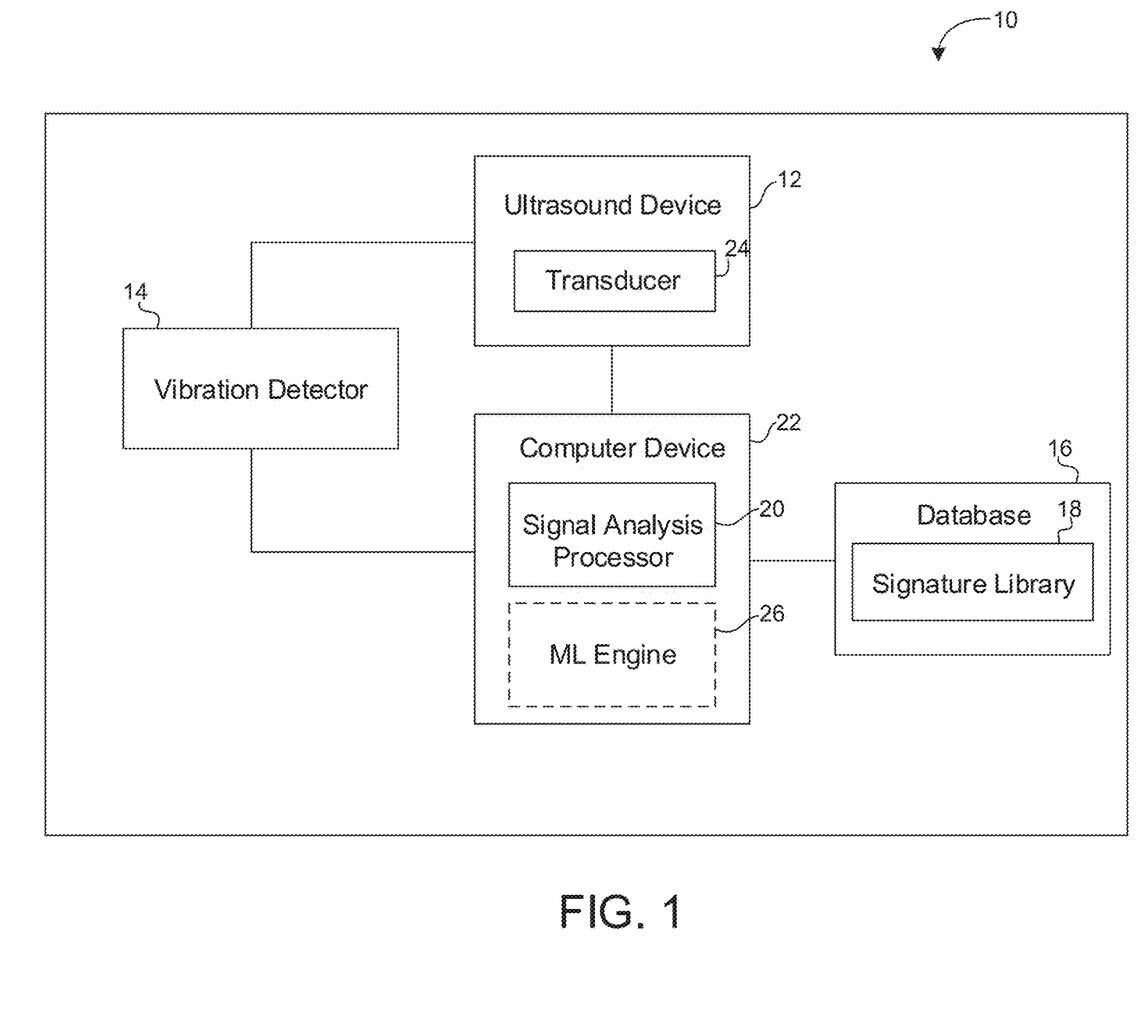
FIG. 1 is a schematic representation of a system for identifying and classifying tissue, according to one embodiment.

Referring now to FIG. 1, an exemplary system 10 for identifying and classifying tissue is shown. As used herein, tissue identity refers to the anatomical structure or organ of the tissue (e.g., heart, liver, skeletal muscle, gall bladder, etc.), and tissue classification refers to the classification of the tissue according to its state or condition (e.g., normal/healthy, abnormal, diseased, injured, cancerous, congenitally defective, etc.). The system 10 may be configured to analyze human body tissue, although it may also be adapted to analyze other types of tissue in alternative embodiments, such as animal tissue.

The system 10 may include an ultrasound device 12 for projecting ultrasound waves at the tissue. In response to stimulation with the ultrasound waves, the examined tissue may absorb some of the ultrasound energy and vibrate, producing a characteristic vibration signature according to its natural harmonic frequency. The system 10 may further include a vibration detector 14 for detecting the vibration signature, and a database 16 storing a signature library 18 of vibration signatures of known tissues having known identities and classifications. As explained in further detail below, a signal analysis processor 20 operating on a computer device 22 may compare the vibration signature of the examined tissue with the stored vibration signatures in the signature library 18 to determine the tissue's identity and classification.

The ultrasound device 12 may include a transducer 24 with piezoelectric elements for producing ultrasound waves at one or more frequencies or amplitudes to stimulate tissue vibration. In some embodiments, the frequency of the ultrasound waves may be fixed at one or more defined frequencies in the ultrasound range (above 20 kilohertz) both for the analysis of the tissue of interest and for creating the signature library 18 of known tissues. In some embodiments, the stimulating ultrasound frequency may range from 1 megahertz (MHz) to 20 MHz. The ultrasound device 12 may be a portable, hand-held machine, although it may be a stationary machine in some embodiments. As non-limiting examples, the ultrasound device 12 may be a Butterfly iQ+ Portable Ultrasound System, a General Electric Healthcare V-Scan Pocket Hand-Held Ultrasound Machine, or a Siemens ACUSON Sequoia Ultrasound System. Other suitable portable or stationary ultrasound machines may be used in other embodiments.

The vibration detector 14 may include a vibration sensor, such as a piezoelectric sensor, for detecting the vibration signature of the tissue of interest. The phrase "vibration signature" as used herein refers to the characteristic vibration signal emitted by the tissue upon ultrasound wave stimulation over a fixed period of time (e.g., 10 milliseconds, 100 milliseconds, 1 second, etc.). Alternatively, the vibration signature may be the characteristic vibration signal emitted by the tissue at different times in response to various ultrasound stimulations. The vibration detector 14 may be included within the computer device 22, or may be electrically connected to or in wireless communication with the computer device 22. For example, in one embodiment in which the computer device 22 is a smartphone or a tablet (e.g., iPad), the vibration detector 14 may include a piezoelectric sensor inside of the smartphone or tablet, and a portable vibration and spectrum analyzer application on the smartphone or tablet. In another embodiment, the vibration detector 14 may be a portable signal analyzer, such as the USB Digital Accelerometer, that is connected to the computer device 22.

The computer device 22 may be in electrical or wireless communication with the ultrasound device 12 and the vibration detector 14 (if the vibration detector 14 is not a part of the computer device 22). The connections between the computer device 22 and the ultrasound device 12 (and the vibration detector 14, if applicable) may be wired connections, such as a USB port connection, or wireless connections, such as Bluetooth or Wi-Fi. In one embodiment, the computer device 22 may be a mobile device, such as a smartphone, a tablet, or a laptop. In other embodiments, the computer device 22 may be a stationary computer, such as a desktop computer.

The signal analysis processor 20 may be software or an application on the computer device 22 having computer-executable instructions for comparing the vibration signature of the tissue of interest with vibration signatures of known tissues (of known identities and classifications) stored in the signature library 18, determining if a match between vibration signatures of the tissue of interest and any of the known tissues in the signature library 18 exists, determining an identity and classification of the tissue based on the known identity and classification of the matching stored vibration signature, and outputting the identity and classification of the tissue of interest at a display interface of the computer device 22 or another computer device (see further details below).

One or more algorithms of the signal analysis processor 20 may be used to determine if the similarity between the vibration signature of the tissue of interest and a stored vibration signature of known tissue in the signature library 18 is above a predetermined threshold indicating that a match is present. As non-limiting examples, the pre-determined threshold may be 70% similar, 80% similar, 90% similar, or 95% similar. The algorithm(s) may apply one or more of time analysis, amplitude analysis, dampening analysis, and/or frequency analysis in its comparison to determine if a match is present, similar to the operation of music matching applications. The comparison analysis may be based on a single degree of freedom, or multiple degrees of freedom. See, for example, "*The Vibration Analysis Handbook*", $2^{nd}$ Edition, by Taylor, James. The vibration signatures of both the tissue of interest and the vibration signatures of the known tissues in the signature library 18 may first undergo various types of processing, such as filtering, before the comparisons are made. Adjustments may be made to make the determination of the degree of similarity more stringent or relaxed. For example, an adjustment making the determination more stringent may be made when the number of matches is large. Conversely, an adjustment making the determination more relaxed may be made when the number of matches is small. Exemplary smartphone and tablet applications suitable for use as the signal analysis processor 20 include, but are not limited to, Vibroscope Lite 4.1, SignalScope X, and VibroChecker.

In some embodiments, the computer device 22 may further include a machine learning (ML) engine 26 that is part of or in communication with the signal analysis processor 20. As explained further below with respect to FIG. 8, the ML engine 26 may apply a machine learning algorithm for predicting an identity and classification of unidentified tissue based on its vibration signature and the vibration signature data of known tissues in the signature library 18.

The database 16 storing the signature library 18 may be accessed locally by the signal analysis processor 20. The database 16 may exist in a memory of the computer device 22, or may be stored externally, such as in a hard disk drive, a flash drive, CD, or DVR. Alternatively, the database 16 storing the signature library 18 may be stored at another location, such as a server or cloud on the Internet that is accessible to the signal analysis processor 20.

Figure 2:
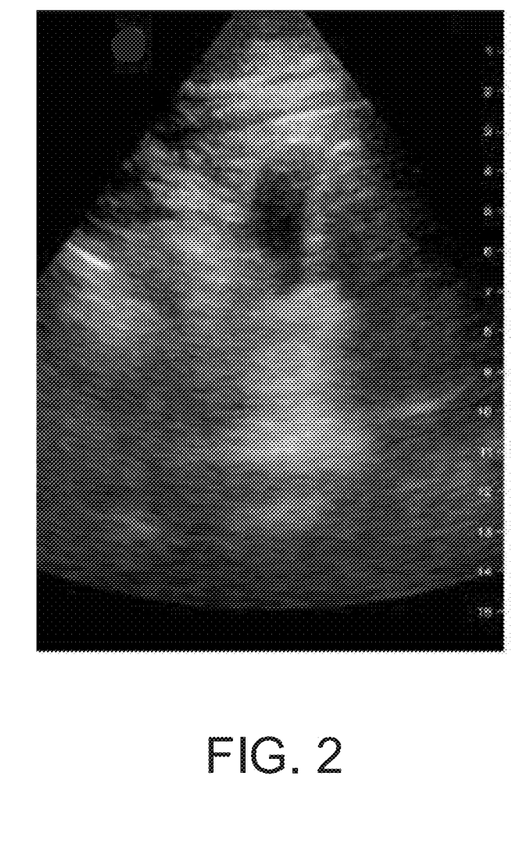
FIG. 2 is an exemplary ultrasound image of liver captured by an ultrasound device of the system of FIG. 1.
Figure 3:
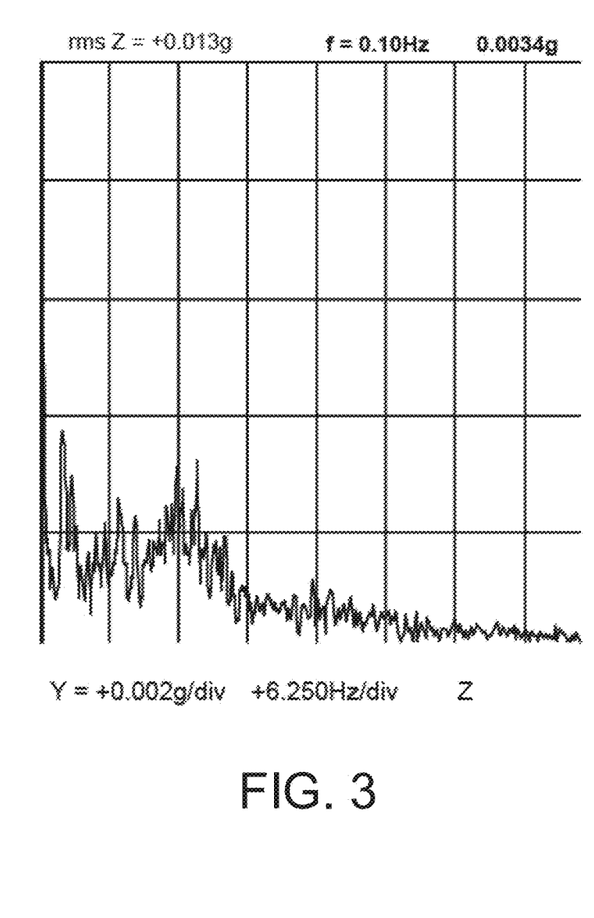
FIG. 3 is an exemplary vibrational signature of liver as captured by a vibration detector of the system of FIG. 1.
Figure 4:
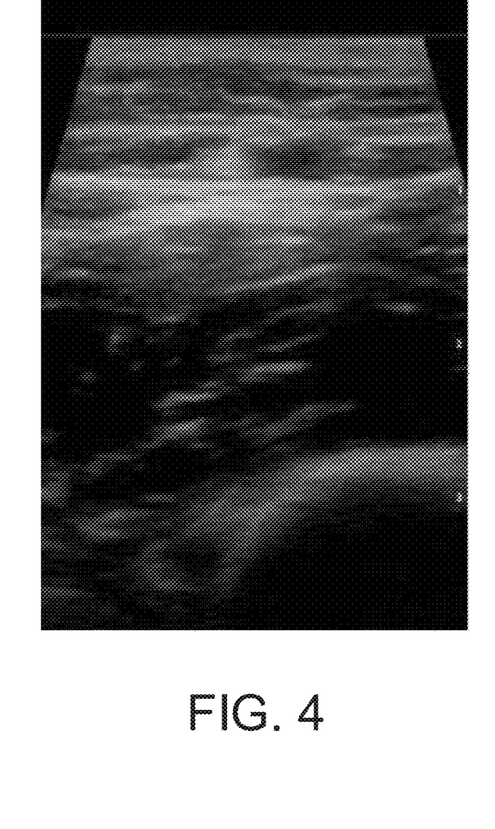
FIG. 4 is an exemplary ultrasound image of skeletal muscle captured by the ultrasound device.
Figure 5:
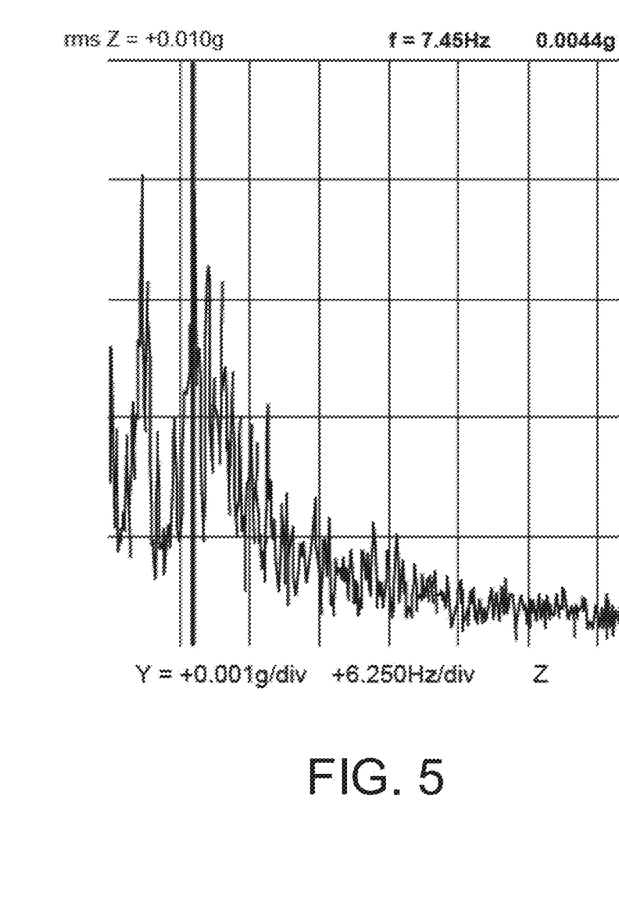
FIG. 5 is an exemplary vibrational signature of skeletal muscle captured by the vibration detector.

FIG. 2 is an ultrasound image of liver captured using a Butterfly iQ+ portable ultrasound system. FIG. 3 is the vibrational signature of the liver produced in response to ultrasound stimulation captured using the USB Digital Accelerometer and the VibroChecker application (as the vibration detector 14). FIG. 4 is an ultrasound image of skeletal muscle tissue captured using a Butterfly iQ+ portable ultrasound system, and FIG. 5 is the vibration signature of the skeletal muscle tissue produced in response to ultrasound stimulation captured using the USB Digital Accelerometer and the VibroChecker application. The vibration signatures of FIGS. 3 and 5 are the vibration signals of the tissues as a function of time after stimulation with ultrasound waves with the ultrasound device.

Figure 6:
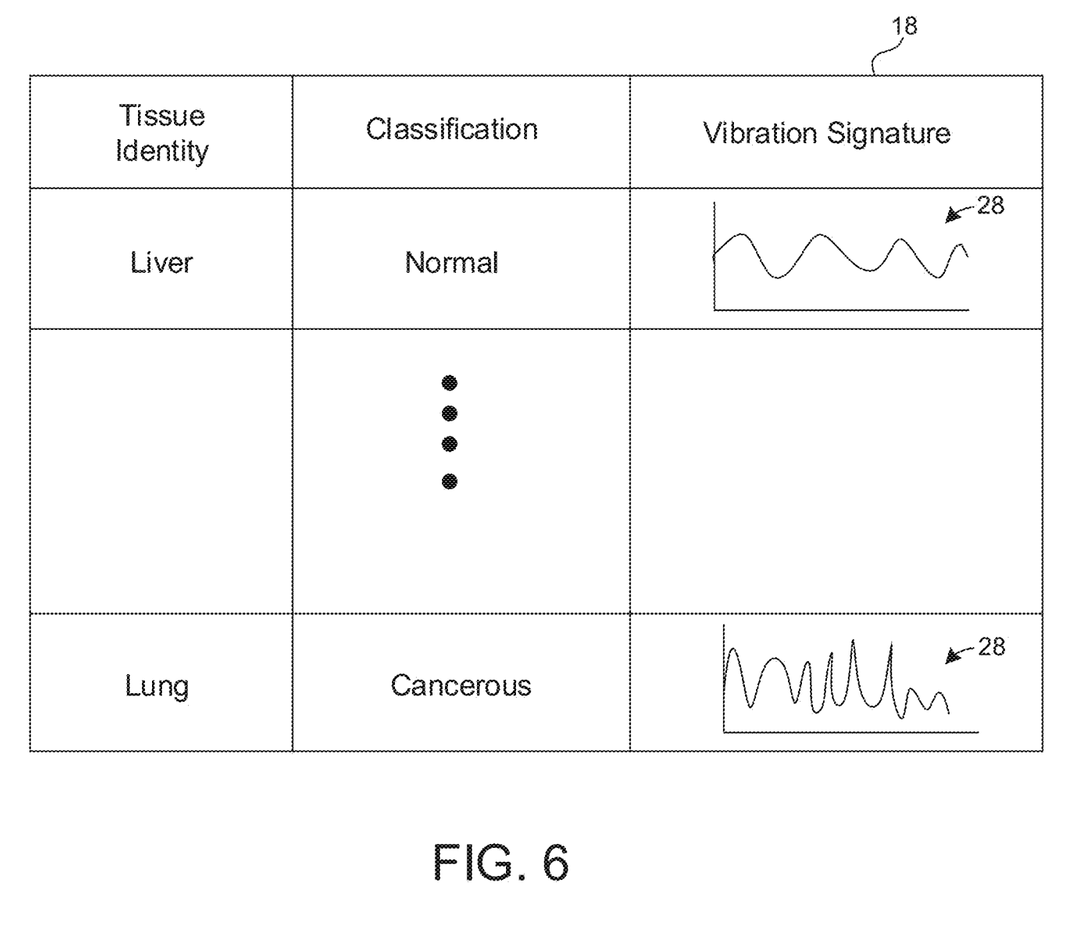
FIG. 6 is an exemplary signature library of the system of FIG. 1, according to one embodiment.

An exemplary signature library 18 is shown in FIG. 6. The signature library 18 may include vibration signatures 28 of known tissues of known identity (e.g., liver, lung, heart, etc.) and classification (e.g., normal, abnormal, injured, diseased, cancerous, etc.). Each vibration signature 28 of the library 18 may be linked with its known tissue identity and classification in the library 18. The signature library 18 may be static, or may be continuously or dynamically updated with new vibration signatures as new tissues are identified and classified by the system 10.

Figure 7:
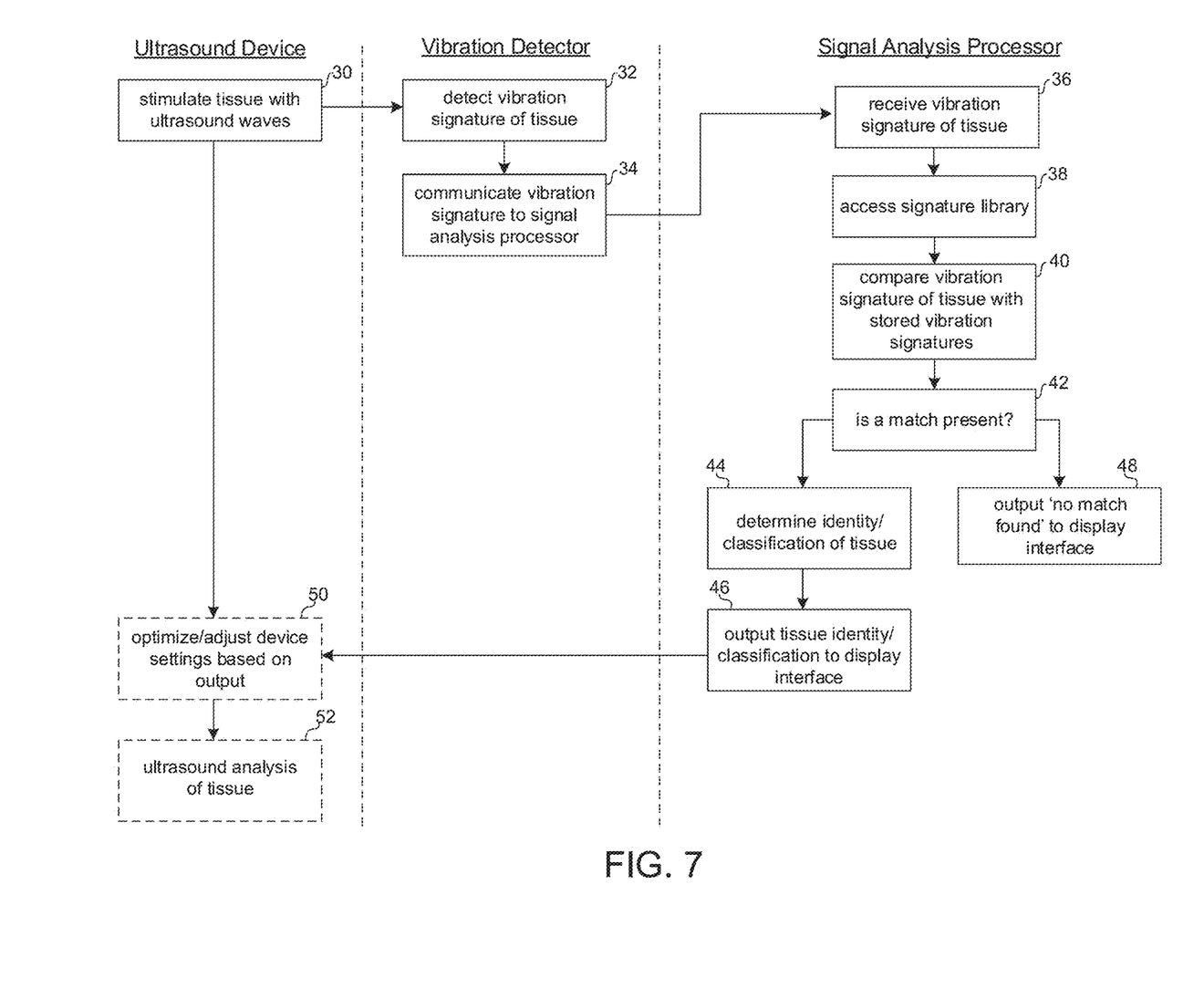
FIG. 7 is a flow chart of an exemplary method for identifying and classifying tissue using the system of FIG. 1, according to one embodiment.

Turning to FIG. 7, an exemplary method of applying the system 10 for identifying and classifying unidentified tissue is shown. The steps of FIG. 7 are organized according to which component of the system 10 (the ultrasound device 12, the vibration detector 14, or the signal analysis processor 20) performs the indicated step. At a first block 30, the unidentified tissue may be stimulated with ultrasound waves of a predefined frequency (or frequency range) using the ultrasound device 12, causing the tissue to vibrate and produce a characteristic vibration signature. The vibration signature may be captured by the vibration detector 14 (block 32), and the vibration detector 14 may communicate the vibration signature to the signal analysis processor 20 for analysis (block 34). The signal analysis processor 20 may receive the vibration signature (block 36), and access the signature library of known tissues for comparison (block 38).

At a block 40, the signature analysis processor 20 may compare the vibration signature of the tissue with the stored vibration signatures of known tissues in the signature library 18 to look for a match. This may involve similarity comparisons using time analysis, amplitude analysis, dampening analysis, and/or frequency analysis to identify a matching vibration signature in the library 18 in which the similarity between the vibration signatures is above a predetermined threshold. In some embodiments, the processor 20 may compare the vibration signature of the unidentified tissue with each of the stored vibration signatures in the signature library 18 to identify one or more matches. In other embodiments, the processor 20 may compare the stored vibration signatures with the vibration signature of the unidentified tissue until a single match is identified, and terminate the comparison once the match is identified. If at least one match is identified (as assessed at a block 42), the processor 20 may determine the identity and classification of the unidentified tissue based on the known identity and classification of the known tissue having the matching stored vibration signature (block 44). For instance, if the matching stored vibration signature is of normal liver tissue, the unidentified tissue will be identified and classified by the processor 20 as normal liver tissue. The determined identity and classification may be output to a display interface of the computer device 22 or another computer device (block 46). In situations in which more than one match is identified, the processor 20 may determine the identity and classification of the tissue based on the stored vibration signature having greatest degree of similarity. Alternatively, the processor 20 may output more than one possible identity and classification for the tissue at the display interface if more than one match is identified. If no match is found, the processor 20 may provide an output indicating that no match is found at the display interface (block 48).

In some embodiments, the tissue identity and classification output may provide feedback to the ultrasound device 12 or a computer system or processor operating the ultrasound device 12, so that the ultrasound parameters or settings of the device 12 may be adjusted or optimized accordingly (block 50). For example, the optimization or adjustment may be carried out automatically via software or an application on the ultrasound device 12 or the computer device 22. The optimized or preferred ultrasound imaging parameters or settings for each tissue type and classification may be stored in the signature library 18 or another storage location accessible to the system 10. Once the parameters are adjusted or optimized, ultrasound imaging of the identified tissue may then be carried out at a block 52 under the optimal or adjusted machine settings. Thus, the identification and classification of the tissue according to its vibration signature may be fed back to the ultrasound device for adjustment/optimization of the ultrasound device settings to improve the quality of the ultrasound images of the tissue. In some embodiments, this feedback may occur in real-time to allow optimization/adjustment of the ultrasound imaging parameters on the fly.

Figure 8:
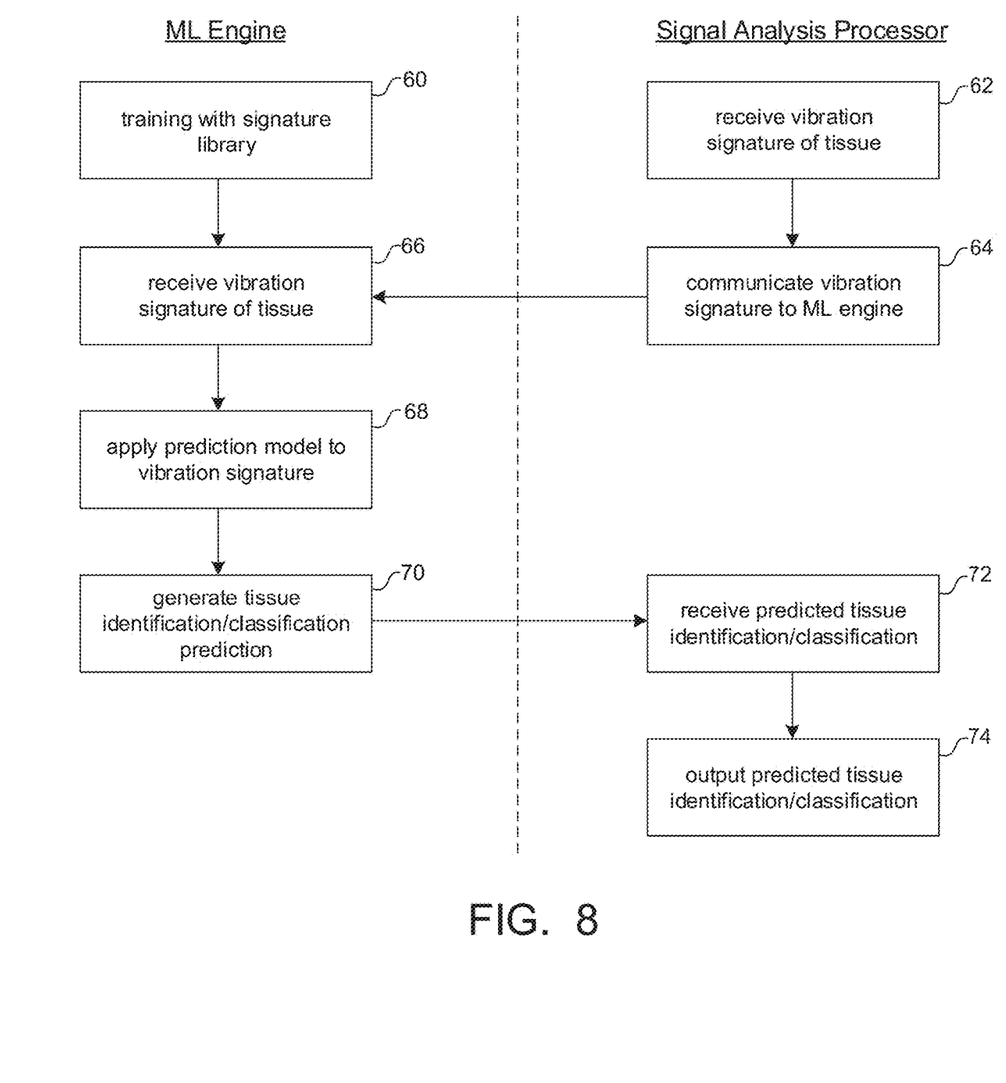
FIG. 8 is flow chart of an exemplary method for predicting the identity and classification of tissue using a machine learning engine of the system of FIG. 1, according to one embodiment.

An exemplary method of predicting the identity and classification of tissue using the ML engine 26 is shown in FIG. 8. The method of FIG. 8 is organized according to steps performed at the ML engine 26 and those performed at the signal analysis processor 20. At a block 60, the ML engine 26 may be trained with data in the signature library 18 which may include target attributes (the identities and classifications of known tissues) and the input data surrounding each target attribute (the vibration signature and its features including time, dampening, amplitude, and frequency features). The block 60 may involve splitting the signature library data into a training set and a test data set, creating a prediction model based on the training data set, validating the prediction model using the test data set, and further refining the prediction model if the prediction model does not accurately predict tissue identity and classification based on the input data in the test data. The prediction model may be refined by splitting the signature library data into different training data sets and test data sets, and as vibration signature data for newly identified and classified tissues are added to the signature library 18.

When an unidentified tissue is analyzed by the system 10, the signal analysis processor 20 may receive its vibration signature from the vibration detector 14 (block 62), and communicate the vibration signature to the ML engine 26 (block 64). In other embodiments, the vibration signature of the unidentified tissue may be directly received at the ML engine 26 from the vibration detector 14. Once received at a block 66, the ML engine 26 may apply the prediction model to the vibration signature of the unidentified tissue (block 68) to generate a prediction of the tissue's identification and classification (block 70). The prediction may be communicated to and received at the signal analysis processor 20 (block 72), and the signal analysis processor 20 may output the predicted tissue identification and classification to a display interface of the computer device 22 or another computer device (block 74). In other embodiments, the ML engine 26 may directly output the prediction to the display interface without communication of the prediction to the signal analysis processor 20.

It is noted that the application of the ML engine 26 as described above may be optional, as the signal analysis processor 20 may determine tissue identity and classification based on vibration signature comparison and analysis alone as described above in relation to FIG. 7. It is further noted that the order of the steps in FIGS. 7-8 is exemplary as the steps may be carried out in different orders or simultaneously in practice.

Figure 9:
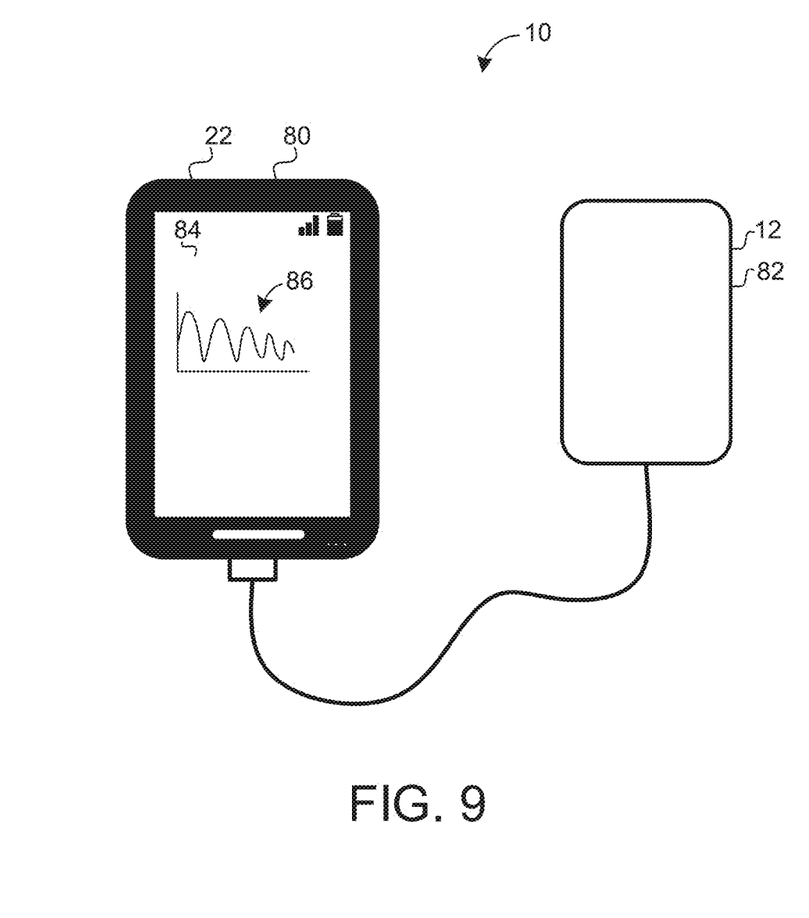
FIG. 9 is an exemplary tissue identification and classification system including a mobile device and a hand-held, portable ultrasound device, according to one embodiment.
Figure 10:
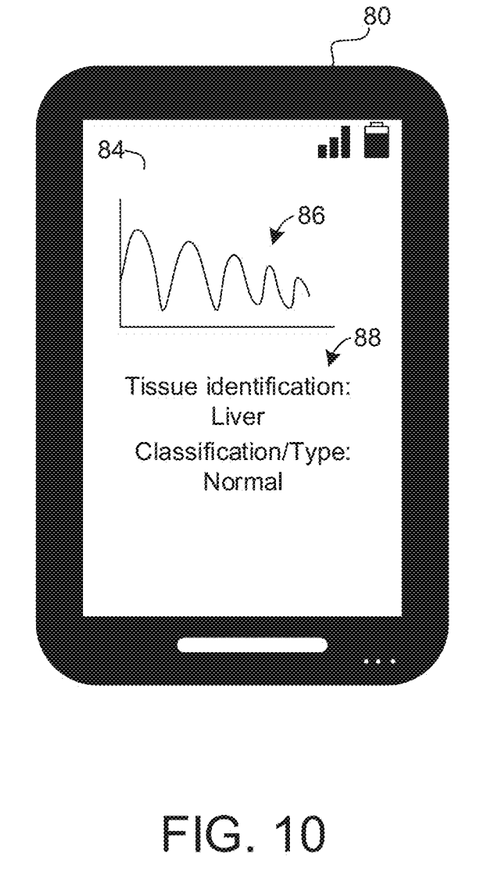
FIG. 10 is an exemplary display interface of a mobile device providing an output of tissue identity and classification as determined using the tissue identification and classification system, according to one embodiment.

An exemplary tissue identification and classification system 10 is shown in FIG. 9. In this embodiment, the computer device 22 is a mobile device 80 (smartphone) and the ultrasound device 12 is a hand-held, portable ultrasound device 82 connected to the mobile device 80 via a USB connection. In this embodiment, the vibration detector 14 includes a piezoelectric sensor inside of the mobile device 80, and a vibration and spectrum analysis application on the mobile device 80. A display interface 84 of the mobile device 80 may display a vibration signature 86 of the tissue of interest. An exemplary display interface 84 of the mobile device 80 displaying the vibration signature 86 and an output 88 of the tissue identity and classification, as determined using the system 10, is shown in FIG. 10.

Figure 11:
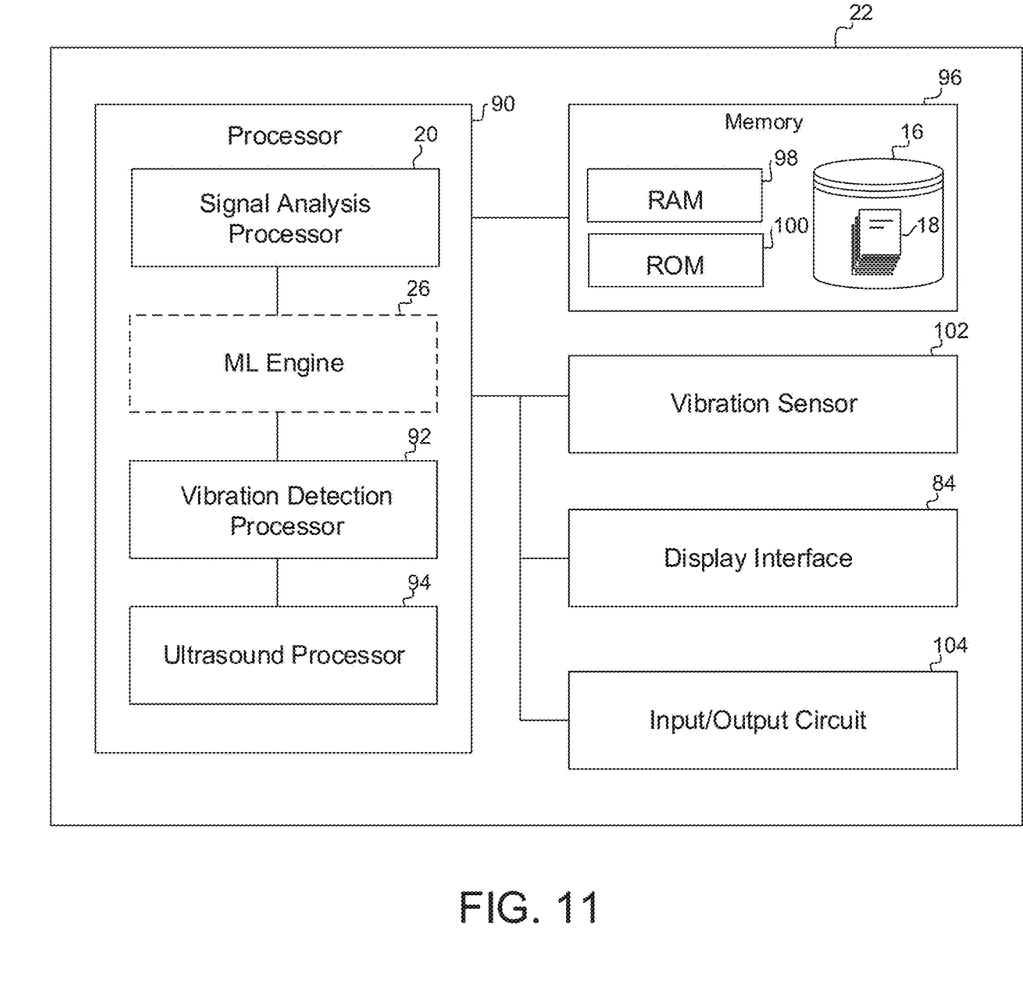
FIG. 11 is a schematic representation of a computer device of the tissue identity and classification system, according to one embodiment.

Certain components of the computer device 22 are schematically depicted in FIG. 11. The computer device 22 may include a processor 90 configured according to computer-executable instructions for performing various functions of computer device 22. In relation to the tissue identification and classification system 10, the processor 90 may include the signal analysis processor 20, a vibration detection processor 92, such as a vibration spectrum and analysis application, and an ultrasound processor 94 for operating the ultrasound device 12 and/or displaying the ultrasound images. In alternative embodiments, either or both of the vibration detection processor 92 and the ultrasound processor 94 may operate on a separate computer device. Optionally, the computer device 22 may further include the ML engine 26 for performing the above-described functions in relation to FIG. 8. A memory 96 may be configured to store the computer-executable instructions for operation of the processor 90 including the signal analysis processor 20, and the vibration detection processor 92, the ultrasound processor 94, and/or the ML engine 26, if present. The memory 96 may include a random access memory (RAM) 98 or volatile memory for temporary storage, and a read-only memory (ROM) 100 or non-volatile memory for permanent storage. The database 16 including the signature library 18 may be stored in the memory 96, or at another location accessible to the signal analysis processor 20, such as a server or cloud on the Internet. A vibration sensor 102, such as a piezoelectric sensor/accelerometer, may be included in the computer device 22 in some embodiments to allow vibration signature detection. Additionally, the computer device 22 may include the display interface 84, as well as an input-output circuit 104 for enabling network communications and communication with other components of the system 10.

The present disclosure provides a technical solution to the problem of identifying and classifying tissue using ultrasound. By recording a tissue's vibrational signature simultaneously while tissue is being examined by ultrasound, the tissue may be identified and classified by comparing its vibration signature to the vibration signatures of known tissues in the signature library. The use of tissue vibration signatures may provide a more objective approach and improve the accuracy of tissue identification/classification compared to ultrasound identification alone, as tissue identification by ultrasound may be subjective and dependent upon the training and experience of the ultrasonographer. Furthermore, the ultrasonographer may use output of the tissue identification and classification system to assist with analysis of the tissue by ultrasound. For example, automatic or manual adjustment or optimization of the ultrasound machine settings (frequency, amplitude, gain, focus, etc.) may be made based on the tissue identification/classification determined by vibration signatures to improve the quality of the ultrasound images of the tissue of interest.

What is claimed is:

1. A system for identifying tissue, comprising:
an ultrasound device having a transducer being configured according to computer-executable instructions for projecting ultrasound waves at tissue to cause the tissue to vibrate and produce vibration signatures of the tissue;
a vibration detector being configured according to computer-executable instructions for detecting produced vibration signatures of the tissue, the produced vibration signatures resulting from the projecting; and
a signal analysis processor in communication with the ultrasound device, the vibration detector, and a database, the signal analysis processor being configured according to computer-executable instructions for:
comparing a first produced vibration signature of the tissue with a plurality of vibration signatures stored in the database, wherein each of the plurality of stored vibration signatures corresponds to an ultrasound wave parameter for a known tissue;
determining a degree of similarity between the first produced vibration signature of the tissue and at least a portion of one or more of the plurality of stored vibration signatures,
determining a match between the first produced vibration signature of the tissue and at least one of the plurality of stored vibration signatures when the degree of similarity is above a predetermined threshold, and
identifying the tissue based on the match.

2. The system of claim 1, further configured according to computer-executable instructions for adjusting the ultrasound waves of the ultrasound device for an optimal ultrasound wave parameter of the known tissue based on the match to produce a second produced vibration signature of the tissue.

3. The system of claim 2, further configured according to computer-executable instructions for matching the second produced vibration signature of the tissue to at least a portion of the optimal ultrasound wave parameter of the known tissue.

4. The system of claim 1, further configured according to computer-executable instructions for splitting the database into a training data set and a test data set.

5. The system of claim 4, further configured according to computer-executable instructions for:
creating a prediction model based on the training data set; and
validating the prediction model using the test data set.

6. The system of claim 5, wherein the instructions for identifying the tissue based on the match include instructions for identifying the tissue based on the prediction model using the first produced vibration signature.

7. The system of claim 6, further configured according to computer-executable instructions for refining the prediction model by splitting the database into a plurality of training data sets and a plurality of test data sets.

8. The system of claim 1, further configured according to computer-executable instructions for determining a classification of the identified tissue based on the match.

9. The system of claim 8, wherein the classification is selected from normal tissue, diseased tissue, cancerous tissue, abnormal tissue, congenitally defective tissue, injured tissue, and damaged tissue.

10. The system of claim 1, wherein the signal analysis processor is further configured according to computer-executable instructions for outputting an identity of the identified tissue to a display interface of a computer device.

11. The system of claim 1, wherein the computer-executable instructions for determining the match between the first produced vibration signature of the tissue and at least one of the plurality of stored vibration signatures when the degree of similarity is above a predetermined threshold includes computer-executable instructions for comparing the produced vibration signature of the tissue with the plurality of vibration signatures stored in the database using one or more of time analysis, amplitude analysis, dampening analysis, and frequency analysis.

12. A method for identifying tissue, the method comprising:
projecting, using an ultrasound device, ultrasound waves at tissue to cause the tissue to vibrate and produce vibration signatures of the tissue;
comparing a first produced vibration signature of the tissue with a plurality of vibration signatures, wherein each of the plurality of vibration signatures corresponds to an ultrasound wave parameter for a known tissue;
determining a degree of similarity between the first produced vibration signature of the tissue and at least a portion of one or more of the plurality of vibration signatures,
determining a match between the first produced vibration signature of the tissue and at least one of the plurality of vibration signatures when the degree of similarity is above a predetermined threshold, and
identifying the tissue based on the match.

13. The method of claim 12, further comprising adjusting the projected ultrasound waves of the ultrasound device for an optimal ultrasound wave parameter of the known tissue based on the match to produce a second produced vibration signature of the tissue.

14. The method of claim 13, further comprising matching the second produced vibration signature of the tissue to at least a portion of the optimal ultrasound wave parameter of the known tissue.

15. The method of claim 12, further comprising splitting the plurality of vibration signatures into a training data set and a test data set.

16. The method of claim 15, further comprising:
creating a prediction model based on the training data set; and
validating the prediction model using the test data set.

17. The method of claim 16, wherein identifying the tissue based on the match includes identifying the tissue based on the prediction model using the first produced vibration signature.

18. The method of claim 12, further comprising determining a classification of the identified tissue based on the match.

19. The method of claim 18, wherein the classification is selected from normal tissue, diseased tissue, cancerous tissue, abnormal tissue, congenitally defective tissue, injured tissue, and damaged tissue.

20. A system for identifying tissue, the system comprising:
an ultrasound device configured to project ultrasound waves at tissue to cause the tissue to vibrate and produce vibration signatures of the tissue;
a vibration detector configured to detect produced vibration signatures of the tissue; and
a signal analysis processor in communication with the ultrasound device, the vibration detector, and a database, the signal analysis processor being configured to:
compare a first produced vibration signature of the tissue with a plurality of known vibration signatures each corresponding to an identity of one or more known tissues,
adjust the projected ultrasound waves to an optimal ultrasound wave parameter for a known tissue when a degree of similarity between the first produced vibration signature and at least a portion of one or more of the plurality of stored vibration signatures for the known tissue is above a predetermined threshold to produce a second produced vibration signature, and
identify the tissue based on comparing the second produced vibration signature to the plurality of known vibration signatures.

\* \* \* \* \*